US011941022B2

(12) United States Patent
Singh et al.

(10) Patent No.: US 11,941,022 B2
(45) Date of Patent: Mar. 26, 2024

(54) SYSTEMS AND METHODS FOR DATABASE SYNCHRONIZATION

(71) Applicant: GE Precision Healthcare LLC, Milwaukee, WI (US)

(72) Inventors: Ravi Raj Singh, Karnataka (IN); Vignesh Doraiswamy, Waukesha, WI (US); Supreeth Dhareshwar, Karnataka (IN); Arindam Dutta Choudhury, Karnataka (IN); Yaxi Shen, Waukesha, WI (US); Shreevatsa Ganapathi, Karnataka (IN)

(73) Assignee: GE PRECISION HEALTHCARE LLC, Milwaukee, WI (US)

( * ) Notice: Subject to any disclaimer, the term of this patent is extended or adjusted under 35 U.S.C. 154(b) by 257 days.

(21) Appl. No.: 17/454,946

(22) Filed: Nov. 15, 2021

(65) Prior Publication Data
US 2023/0153320 A1 May 18, 2023

(51) Int. Cl.
*G06F 16/20* (2019.01)
*G06F 16/27* (2019.01)
*G16H 10/60* (2018.01)
*G16H 30/20* (2018.01)

(52) U.S. Cl.
CPC .......... *G06F 16/27* (2019.01); *G16H 10/60* (2018.01); *G16H 30/20* (2018.01)

(58) Field of Classification Search
CPC ......... A61B 6/032; A61B 6/566; G06F 16/27; G06T 11/60; G06T 17/00; G16H 10/60; G16H 30/20; G16H 30/40; G16H 50/20
See application file for complete search history.

(56) References Cited

U.S. PATENT DOCUMENTS

| 7,613,835 | B2 | 11/2009 | Sato |
| 9,524,327 | B2 | 12/2016 | Kang et al. |
| 2010/0205597 | A1* | 8/2010 | Bender .................... G06F 8/65 707/610 |
| 2011/0113013 | A1* | 5/2011 | Reddy ................ G06F 11/1453 707/646 |
| 2018/0144822 | A1 | 5/2018 | Guendel et al. |
| 2018/0308566 | A1* | 10/2018 | Dempers ................ G06F 16/27 |
| 2019/0108903 | A1 | 4/2019 | Kalafut et al. |
| 2020/0117681 | A1* | 4/2020 | Greenlee .............. G06F 16/273 |
| 2021/0158933 | A1* | 5/2021 | Frosch ................... G16H 40/67 |
| 2021/0193331 | A1 | 6/2021 | Raman et al. |

FOREIGN PATENT DOCUMENTS

WO 2021108398 A1 6/2021

* cited by examiner

*Primary Examiner* — Mahesh H Dwivedi
(74) *Attorney, Agent, or Firm* — McCoy Russell LLP

(57) ABSTRACT

Methods and systems are provided for data synchronization. In one example, a method for synchronizing data between an agent and a core includes sending, from the agent, a request to the core identifying a data subset to be synchronized, the request further including a fingerprint for each block of data in the data subset; receiving, at the agent, a response from the core identifying a block of mismatched data between the core and the agent; fetching a fingerprint for each record of the identified block of mismatched data and creating a fingerprint of the block based on the fetched fingerprints; sending, from the agent, a request to the core including the fingerprint of the block; and receiving, at the agent, one or more records from the core identified via a comparison of fingerprints of the one or more records.

20 Claims, 10 Drawing Sheets

SYSTEMS AND METHODS FOR DATABASE SYNCHRONIZATION

FIELD

Embodiments of the subject matter disclosed herein relate to database synchronization, and more particularly to automatic database synchronization with medical imaging modalities.

BACKGROUND

Medical imaging may be performed to diagnose or rule out a patient condition. Medical imaging modalities such as computed tomography (CT) scanners may communicate with servers to enable various functions to be performed, such as image reconstruction and/or storage and scan protocol optimization.

One challenge in managing information that is communicated between a core system (e.g., a server) and an agent system (e.g., a medical imaging modality) is data synchronization, where information stored or available at the agent system is maintained in sync with information stored on the core system. Data synchronization may depend on establishing and maintaining a persistent connection between the core and the agent, and may entail using additional/specific protocols such as Point-to-Point Tunneling Protocol (PPTP) or Secure Socket Tunneling Protocol (SSTP). Different security restraints may be imposed on the core and the agent. A synchronizing algorithm may rely on exchanging large volumes of data between the core and the agent to identify differences or mismatches in the data, and failover management may not be efficient or robust. As a result of these and other issues, synchronizing data may entail intensive resource utilization, which may impact other connected systems and networks and may increase a cost of maintaining communications infrastructure. Additionally, a data synchronization process may rely on manual intervention, resulting in longer examination times and increasing a probability of operator error.

BRIEF DESCRIPTION

In one embodiment, a method for synchronizing data between an agent and a core includes sending, from the agent, a request to the core identifying a data subset to be synchronized, the request further including a fingerprint for each block of data in the data subset; receiving, at the agent, a response from the core identifying a block of mismatched data between the core and the agent; fetching a fingerprint for each record of the identified block of mismatched data and creating a fingerprint of the block based on the fetched fingerprints; sending, from the agent, a request to the core including the fingerprint of the block; and receiving, at the agent, one or more records from the core identified via a comparison of the fingerprints of the one or more records.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
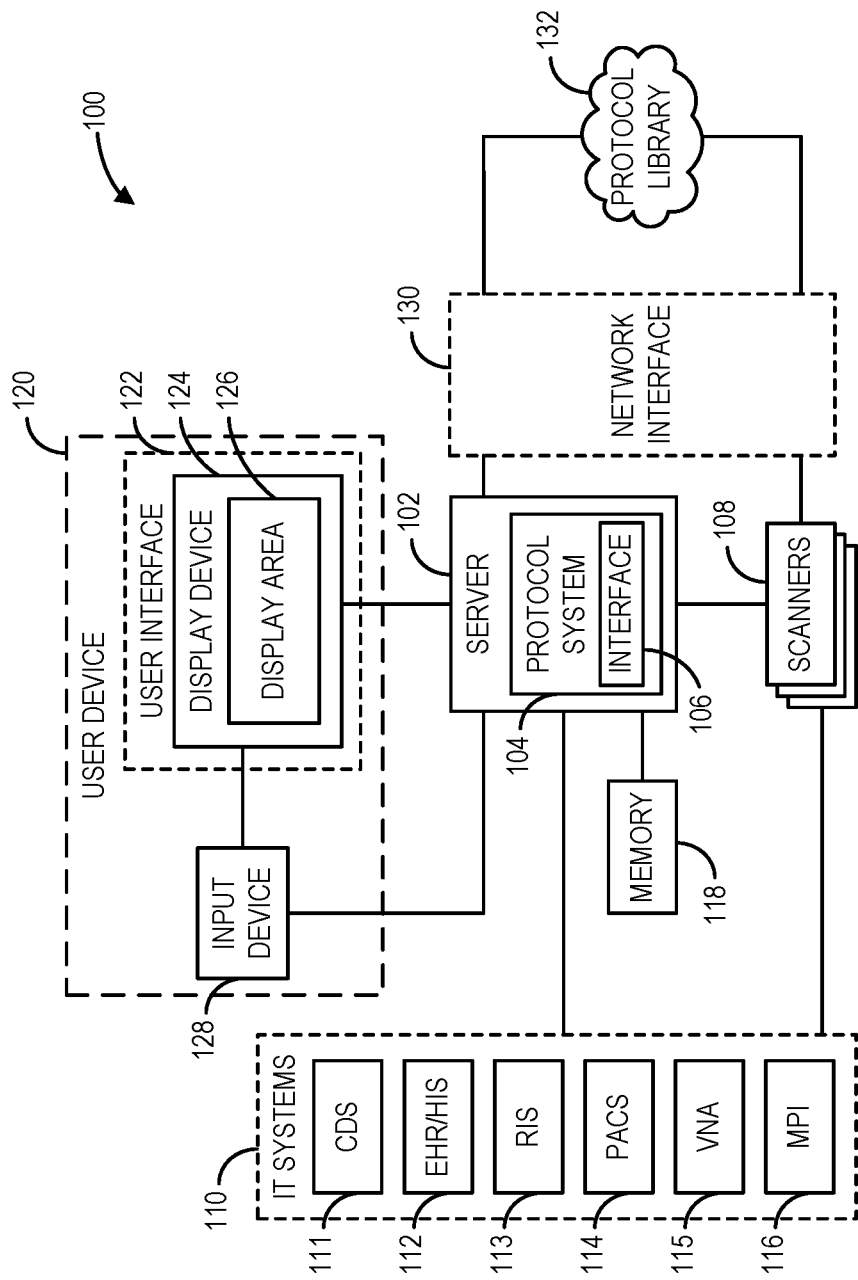
FIG. 1 shows a schematic block diagram of an exemplary medical imaging system, according to an embodiment.
Figure 2:
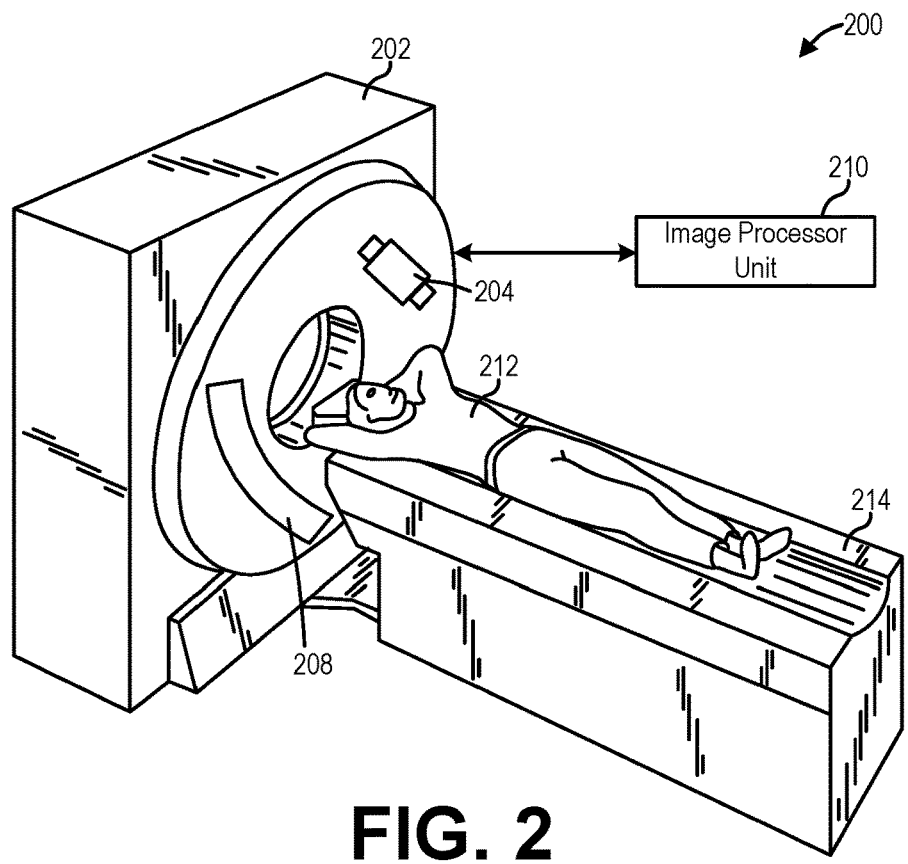
FIG. 2 shows a pictorial view of an exemplary computed tomography (CT) imaging system, according to an exemplary embodiment.
Figure 3:
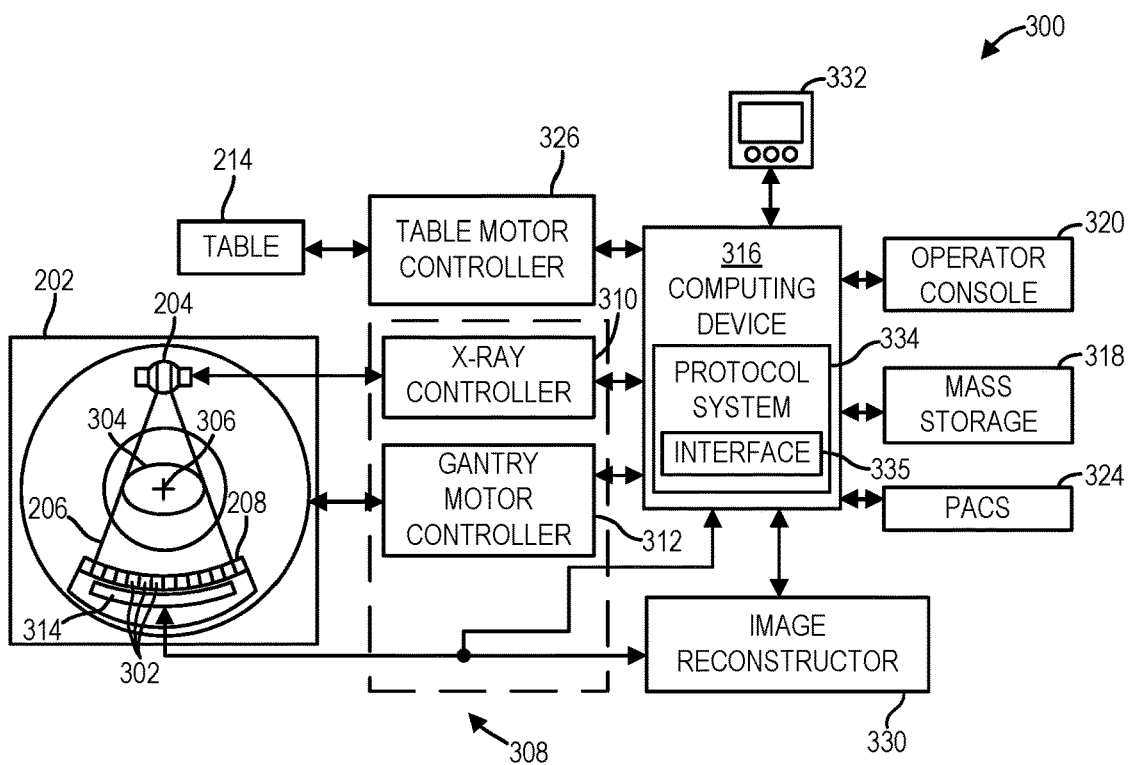
FIG. 3 shows a schematic block diagram of the exemplary CT imaging system, according to an exemplary embodiment.

The following description relates to various embodiments of database synchronization, and in particular database synchronization in a medical imaging environment. One such medical imaging system employing the database synchronization disclosed herein is depicted in FIG. 1. It will be appreciated that in some examples, the database synchronization may be configured to operate under a client-server framework where information may be passed between a core, which may be a server or other external computing device, and an agent (e.g., a client program), which may be installed on an imaging modality. One such example of an imaging modality is a computed tomography (CT) imaging system, as depicted in FIGS. 2 and 3.

Figure 4:
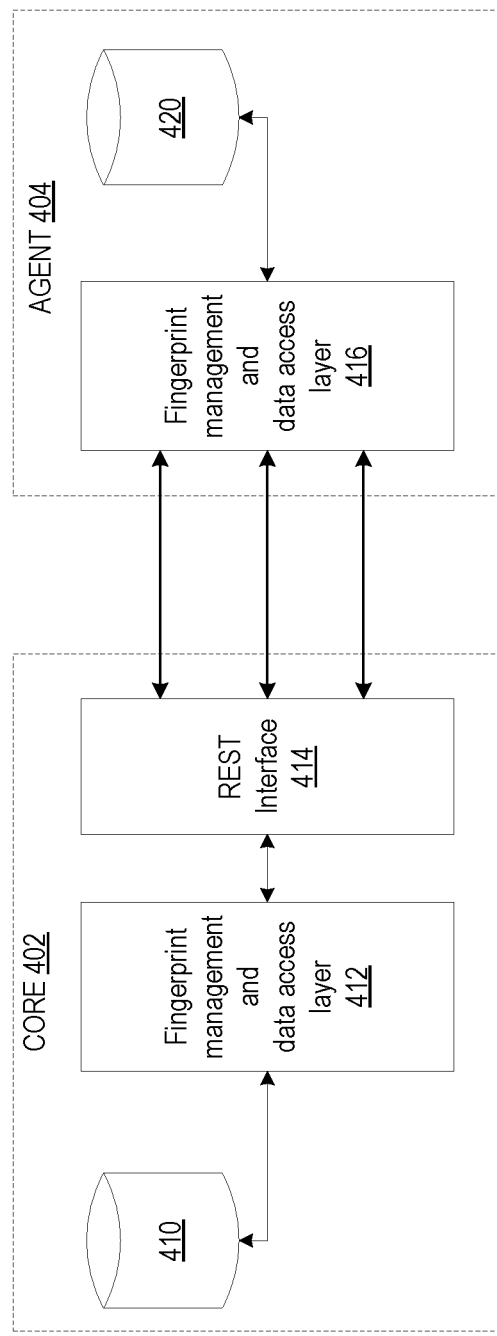
FIG. 4 shows a schematic diagram illustrating an example system architecture for database synchronization between an agent and a core.

The database synchronization may be implementable on a system architecture, such as the exemplary system architecture of FIG. 4. Exemplary workflows for the database synchronization are depicted in FIGS. 5-11.

Referring now to FIG. 1, a block diagram of an example system 100 is depicted according to an embodiment. In the illustrated embodiment, the system 100 is a medical imaging system implementing multiple imaging modalities on respective scanners 108. It will be appreciated that embodiments set forth herein may implement any number of scanners 108. A CT imaging system, such as in the CT imaging system of FIGS. 2 and 3, in one example of a scanner 108. It will be understood that still other embodiments may not actively acquire medical images. Instead, such embodiments may retrieve images or imaging data that was previously acquired by an imaging system and analyze the imaging data as set forth herein.

As shown, the system 100 may include multiple components. The components may be coupled to one another to form a single structure, may be separate but located within a common room, or may be remotely located with respect to one another. For example, one or more of the modules described herein may operate in a data server that has a distinct and remote location with respect to other components of the system 100, such as at least one of the scanners 108 and a user device 120. Optionally, the system 100 may be a unitary system that is capable of being moved (e.g., portably) from room to room. For example, the system 100 may include wheels or be transported on a cart.

In the illustrated embodiment, a server 102 may be a computing device configured to interface with other components of the system 100 (e.g., via an interface 106). As such, the server 102 may be configured to control operation of the system 100. In embodiments described herein, the server 102 may implement one or more intelligent automated systems, such as, for example, a protocoling recommendation system 104 configured to automatically recommend scan protocols based on received medical data. While the protocoling recommendation system 104 is described herein for illustrative purposes, it should be appreciated that the systems and methods described herein may also be used with other and/or different recommendation systems or different types of automated systems without departing from the scope of this disclosure.

The protocoling recommendation system 104 may be operable to translate selected scan protocols to scan protocol executables for initiating a scan session at at least one of the scanners 108. In some embodiments, the protocoling recommendation system 104 may automatically recommend, select, and translate the scan protocols for initiating the scan session upon receiving an input including the medical data (e.g., a scan order, clinical indications, patient medical histories, prior exam images, prior reports, etc.). In additional or alternative embodiments, the protocoling recommendation system 104 may recommend and display scan protocols (e.g., at a display area 126 of a display device 124) and may then await confirmation from one or more medical professionals for selection and/or translation of the recommended protocols. The protocoling recommendation system 104 may accordingly include the interface 106 for receiving and transmitting the medical data and the recommended scan protocols or scan protocol executables.

In various embodiments, the server 102 may take the form of a mainframe computer, server computer, desktop computer, laptop computer, tablet device, network computing device, mobile computing device, mobile communication device, etc. In one embodiment, the server 102 may take the form of an edge device for interfacing between the user device 120, the scanners 108, information technology (IT) systems 110, a master protocol library 132, etc.

The protocoling recommendation system 104 may take the form of a logic subsystem including one or more physical devices configured to execute one or more instructions. For example, the protocoling recommendation system 104 may be configured to execute one or more instructions that are part of one or more applications services, programs, routines, libraries, objects, components, data structures, or other logical constructs. Such instructions may be implemented to perform a task, implement a data type, transform a state of one or more devices, or otherwise arrive at a desired result.

The protocoling recommendation system 104 may include one or more processors configured to execute software instructions. In additional or alternative embodiments, the protocoling recommendation system 104 may include one or more hardware or firmware logic machines configured to execute hardware or firmware instructions. The one or more processors may be single- or multi-core, and programs executed thereon may be configured for serial or parallel or distributed processing. The protocoling recommendation system 104 may optionally include individual components distributed throughout two or more devices corresponding to the server 102, where the two or more devices may be remotely located and/or configured for coordinated processing. Further, one or more aspects of the protocoling recommendation system 104 may be virtualized and executed by remotely accessible networked computing device configured in a cloud computing configuration.

The server 102 may be in communication with a memory 118, either included in a computing device corresponding to the server 102 or may be a separate device communicably coupled to the server 102. Accordingly, the memory 118 may include removable media and/or built-in devices. Specifically, the memory 118 may include one or more physical, non-transitory devices configured to hold data and/or instructions executable by the protocoling recommendation system 104 to implement the herein described methods. When such methods are implemented, a state of the memory 118 may be transformed (for example, to hold different, or altered, data).

In some embodiments, the memory 118 may include optical memory (e.g., configured to read compact discs (CDs), digital versatile discs (DVDs), high-definition DVDs (HD-DVDs), Blu-ray discs, etc.), magnetic memory devices (e.g., hard drive disks, floppy disk drives, tape drives, magnetoresistive random-access memory (MRAM), etc.), and the like. In some embodiments, the intelligent automated protocoling system 104 and the memory 118 may be integrated into one or more common devices, such as an application-specific integrated circuit or a system on a chip. It will be appreciated that the memory 118 may be a non-transitory storage medium.

The server 102 may further be communicably coupled with IT systems 110, where the IT systems 110 may include one or more clinical decision support systems (CDS) 111, electronic health or medical records and/or hospital information systems (EHR/HIS) 112, radiological information systems (RIS) 113, picture archiving and communications systems (PACS) 114, vendor neutral archives (VNA) 115, master patient indices (MPI) 116, etc. Each of the IT systems 110 may provide the server 102 with medical data relevant to a scan order queried at the user device 120. As an example, medical data corresponding to the scan order (e.g., clinical indications, patient medical histories, patient allergies, etc.) may be selected by a medical professional operating the user device 120, and the medical data may be retrieved from the EHR/HIS 112. As another example, upon receiving the scan order, the intelligent automated protocoling system 104 may enter free text in the EHR/HIS 112 or select further medical data (e.g., prior reports, modality worklists, prior exam images, etc.) from the RIS 113 and/or the PACS 114. In some embodiments, the scanners 108 may also be communicably coupled to the IT systems 110, and may similarly receive medical data therefrom (for example, the scanners 108 may receive modality worklists from the RIS 113).

The server 102 and the scanners 108 may be communicably coupled to one another. In some embodiments, each of the scanners 108 may correspond to a different imaging modality (e.g., x-ray, magnetic resonance (MR), ultrasound (US), CT, positron emission tomography (PET), single-photon emission CT (SPECT), and combinations thereof, e.g., multi-modality imaging, such as PET/CT, PET/MR, SPECT/CT, etc.). In other embodiments, each of the scanners 108 may correspond to the same imaging modality, whereby each of the scanners 108 may be located in a separate room (e.g., in a hospital) or in separate facilities (e.g., hospitals) altogether. In still other embodiments not depicted at FIG. 1, the system 100 may include only one scanner 108 directed to a single imaging modality (e.g., such as in the CT imaging system as described below with reference to FIGS. 2 and 3).

Additional resources available to the server 102 and/or the scanners 108 may be stored on a longer-term storage device or network (e.g., a cloud-based computing device or server), such as, for example, a master protocol library 132. However, it will be appreciated that the master protocol library 132 and/or other resources of the additional resources may be stored on any known data storage medium, for example, a permanent storage medium, removable storage medium, and the like. As such, it will be appreciated that the master protocol library 132 may be stored on a non-transitory storage medium. It will be appreciated that the scanners 108 and/or remote devices (not shown) may have access to the master protocol library 132 and/or the other resources. For example, the scanners 108 and/or remote devices may be enabled to periodically update the master protocol library 132 by adding, removing, substituting, or otherwise altering scan protocols stored on the master protocol library 132 (for example, in the case of the scanners 108, the periodic updating may be based on newly received and executed scan protocols).

Each of the server 102 and the scanners 108 may be communicably coupled to the master protocol library 132. In embodiments wherein the server 102 and/or the scanners 108 remotely access the master protocol library 132 over a network, communications therebetween may occur across a network interface 130 (e.g., a firewall). For example, the server 102 and/or the scanners 108 may communicate with and/or across the network in a wired and/or wireless manner via the network interface 130. The network may be a wireless telephone network, a wireless local area network, a wired local area network, a wireless wide area network, a wired wide area network, etc. In some embodiments, the network interface 130 may allow messages to be sent and/or received to and/or from other devices or entities, such as the master protocol library 132, via the network (e.g., the public Internet). In some embodiments, the network may be regarded as a private network connection and may include, for example, a virtual private network or an encryption or other security mechanism employed over the public Internet.

The protocoling recommendation system 104 may recommend scan protocols to be executed by the at least one of the scanners 108. The at least one of the scanners 108 may then receive the recommended scan protocols as executables from the server 102, whereby a scan session may be initiated. In some embodiments, a medical professional may instead manually query a scan protocol, which may be directly received by the at least one of the scanners 108 from the master protocol library 132, and the scan session may be initiated therefrom. It will be appreciated that when a scan protocol has been selected and executed, regardless of whether the scan protocol has been recommended by the protocoling system 104 or the scan protocol has been manually provided by the medical professionals, the protocoling recommendation system 104 may update the master protocol library 132, a master protocol mapping library (e.g., on the memory 118 of the server 102), and/or a local protocol mapping library (e.g., on the at least one of the scanners 108) based on the selected and executed scan protocol. Additionally, one or more data synchronization algorithms may be used to synchronize and maintain data consistency between the local, master, and global protocol mapping libraries, as described in greater detail herein.

In operation, the server 102 may acquire medical data (e.g., from the IT systems 110) and imaging data (e.g., from the scanners 108), which may be translated for display to an operator or user (e.g., the medical professional) on the display device 124. As an example, the medical data may be transformed into and displayed at the display device 124 as a user-facing graphical and/or textual format, which may be standardized across all user devices 120 or may be particular to a given facility, department, profession, or individual user. As another example, the imaging data (e.g., three-dimensional (3D) volumetric data sets, two-dimensional (2D) imaging slices, etc.) may be used to generate one or more images at the server 102 or the user device 120, which may then be displayed to the operator or user at the display device 124.

In some embodiments, the server 102 may be communicably coupled to the display device 124 via a user interface 122 that enables an operator to control at least some operations of the system 100. The user interface 122 may include hardware, firmware, software, or a combination thereof that enables an individual (e.g., the operator) to directly or indirectly control operation of the system 100 and the various components thereof. As shown, the user interface 122 may include the display device 124, the display device 124 including the display area 126. In some embodiments, each of the server 102 and the user interface 122 may be operably connected to one or more user interface input devices 128, such as a physical keyboard, mouse, and/or touchpad. As an example, a touchpad may be configured to the server 102 and the display area 126, such that when a user moves a finger/glove/stylus across a face of the touchpad, a cursor atop a displayed medical record, image, etc. on the display device 124 may move in a corresponding manner.

In an exemplary embodiment, the display device 124 is a touch-sensitive display (e.g., touchscreen) which may detect a presence of a touch from the operator on the display area 126 and may also identify a location of the touch in the display area 126. The touch may be applied by, for example, at least one of the operator's hand, glove, stylus, or the like. As such, the touch-sensitive display may also be characterized as an input device that is configured to receive inputs from the operator (such as a queried medical procedure).

The display device 124 may communicate information from the server 102 to the operator by displaying the information to the operator. The display device 124 and/or the user interface 122 may also communicate audibly. The display device 124 may be configured to present information to the operator immediately before, during, and after the scan session. The information presented may include formatted medical records, images from one or more of the scanners 108, graphical elements, measurement graphics of displayed images, user-selectable elements, user settings, and other information (e.g., administrative information, other personal information of a patient, and the like).

As shown in FIG. 1, the user device 120 may include at least some of the components of the system 100 (e.g., the user interface 122, the display device 124, the display area 126, the input device 128, etc.). In some embodiments, the user device 120 may take the form of one or more of a mainframe computer, server computer, desktop computer, laptop computer, tablet device, network computing device, mobile computing device, mobile communication device, etc. In some embodiments, the user device 120 may be a personal mobile device interfacing with the server 102 via an application stored thereon. In other embodiments, the user device 120 may not be a single physical device, and the various components thereon may be associated with other aspects of the system 100. As an example, a single device may include the server 102, the user interface 122, the display device 124, the display area 126, and the input device 128. As another example, the user interface 122, the display device 124, the display area 126, and the input device 128 may be integrated with one of the scanners 108.

The server 102 or the user device 120 may implement an image-processing module which may receive imaging data from a given scanner 108 and then process the imaging data. For example, the image-processing module may process 3D volumetric imaging data to generate 2D image slices for displaying to the operator of the system 100. Similarly, the image processing module may process the imaging data to generate 3D renderings for displaying to the operator. It will be appreciated that acquired imaging data may be processed in real-time during a scanning session as signals are received at the given scanner 108. Additionally or alternatively, the imaging data may be stored temporarily in the memory 118 during the scanning session and processed in less than real-time in a live or off-line operation.

In addition to the image-processing module, the server 102 or the user device 120 may also include one or more of a graphics module, an initialization module, a tracking module, and an analysis module. The image-processing module, the graphics module, the initialization module, the tracking module, and the analysis module may coordinate with one another to present information to the operator during and after the scanning session. For example, the image-processing module may be configured to display an acquired image on the display device 124, and the graphics module may be configured to display designated graphics along with the displayed image, such as selectable icons and measurement parameters relating to the image.

A screen of the display area 126 of the display device 124 may be made up of a series, or matrix, of pixels which display the imaging data acquired with the scanners 108. The acquired imaging data may include one or more imaging parameters calculated for each pixel, or group of pixels (for example, a group of pixels assigned the same parameter value), of the display, where the one or more calculated image parameters may include one or more of an intensity, velocity (e.g., blood flow velocity), color flow velocity, texture, graininess, contractility, deformation, and rate of deformation value. The series of pixels may then make up the displayed image generated from the acquired imaging data.

In some embodiments, the server 102 or the memory 118 may include an adaptive learning module which includes one or more models (e.g., Gaussian model, deep neural network) and instructions for performing adaptive learning functionalities. For example, the recommendation system 104 may interface (e.g., via the interface 106) to the adaptive learning module such that the recommendation system may adaptively "learn" and recognize patterns in a series of executed scan protocols over time. As such, the recommendation system 104 may be configured to periodically update the adaptive learning module and/or data utilized by the adaptive learning module such that protocol recommendations may be made more consistent over time (in that medical expertise is accumulated over continued use of the system 100), thereby incrementally improving patient experience and health outcomes. As such, it will be appreciated that the recommendation system 104 and the IT systems 110 may update information related to medical scanning procedures in an asynchronous manner, allowing the recommendation system 104 to analyze and generate different, but related, data structures to those stored on the IT systems 110.

In general, numerous manual steps are included in a workflow for assigning a scanning protocol, initiating a scan session based on the scanning protocol, and acquiring images therefrom. When a patient arrives at a medical facility to diagnose a medical issue, an order may be placed by a clinician to a radiologist. The radiologist may then query data from multiple IT systems and may generate a radiologist-level scan protocol. The radiologist-level scan protocol may then be translated to a scanner-level scan protocol by a technologist. The scanning protocols and/or other information specific to a certain procedure and/or a certain subject (or subject type/classification) may be stored, updated, and maintained in more than one location.

For example, an order level protocol for a subject receiving a scan may be selected from a pre-established list of generic protocols, and stored as a setting in a first (e.g., administrative) database hosted on the server 102. A radiologist may generate a more specific radiologist-level protocol based on the order level protocol and subject information, which may be stored in a master protocol mapping library in a second database hosted on the server 102. A technologist may generate a scanner-level protocol based on the radiologist-level protocol, scanner information, and/or additional subject information received from the subject at the time of the examination, which may be stored in a local protocol mapping library of a memory of a scanner 108.

In some examples, one or more scanner-level protocols may be recommended by the protocoling recommendation system 104 in order to minimize radiologist and/or scan technologist workflow demands. The protocols may be recommended based on historical selection data (e.g., past protocols executed for various procedures) and/or patient demographic data, each of which may be communicated from the scanners to the server 102/protocoling recommendation system 104. In order to minimize data mismatches between different systems or databases and ensure data consistency, one or more data synchronization procedures may be used.

However, the data synchronization procedures may be costly in terms of resources and may increase an amount of manual intervention, increasing network traffic and slowing down examinations. For example, an intelligent automated protocoling recommendation system may be in communication with one or more scanners, each scanner corresponding to any one of a plurality of medical imaging modalities. For a first scan of a subject, the protocoling recommendation system may automatically generate and assign protocol recommendations for the first scan, and may then automatically select a scan protocol and a scanner therefor, or may await manual confirmation or selection of the scan protocol from the protocol recommendations by a medical professional (e.g., a radiologist). The protocoling recommendation system may store or update the protocol recommendations for the first scan in a master protocol mapping library on the server 102. The protocoling recommendation system may then update a protocol mapping library based on the selection (e.g., which protocol was ultimately selected by the medical professional).

In this way, data synchronization may occur between one or more scanners and the server/protocol recommendation system. As explained previously, the data synchronization may be prone to challenges owing to communication protocol demands, persistent connection demands, security restraints, and the like, which may slow down data synchronization or may result in delayed or lost data. Thus, according to embodiments disclosed herein, a custom protocol layered over traditional REST APIs may be deployed to enable a core and agent interaction (e.g., server and scanner interaction) that can synchronize the data across the modality systems. The architecture leverages REST principles and implementation to achieve a robust data synchronization.

As discussed with reference to FIG. 1, in some embodiments, the recommendation system (e.g., 104) may be configured to interface with a plurality of scanners (e.g., 108), such that the recommendation system may recommend scan protocols for more than one scanner and/or more than one imaging modality. However, in other embodiments, the recommendation system may be configured to interface with one or more scanners corresponding to only one imaging modality. That is, in some embodiments, the medical imaging system described herein may be directed to a specific imaging modality. In either example, FIGS. 2 and 3 provide an exemplary CT imaging system that may be coupled to or incorporate an exemplary embodiment of the recommendation system as described herein.

Referring now to FIG. 2, an exemplary system 200 configured for CT imaging is depicted. Specifically, the system 200 may be configured to image a subject 212 such as a patient, an inanimate object, one or more manufactured parts, and/or foreign objects such as dental implants, stents, and/or contrast agents present within the body. In one embodiment, the system 200 includes a gantry 202, which in turn, may further include at least one x-ray source 204 configured to project a beam of x-ray radiation 206 (see FIG. 3) for use in imaging the subject 212 laying on a table 214. Specifically, the x-ray source 204 may be configured to project the x-rays 206 towards a detector array 208 positioned on the opposite side of the gantry 202. Although FIG. 2 depicts only a single x-ray source 204, in certain embodiments, multiple x-ray sources and/or detectors may be employed to project a plurality of x-ray radiation beams 206 for acquiring projection data at different energy levels or angular orientations corresponding to the subject 212. In some embodiments, the x-ray source 204 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the system 200 further includes an image processor unit 210 configured to reconstruct images of a target volume of the subject 212 using an iterative or analytic image reconstruction method, or a combination of both. For example, the image processor unit 210 may use an analytic image reconstruction approach such as filtered backprojection (FBP) to reconstruct images of a target volume of the patient. As another example, the image processor unit 210 may use an iterative image reconstruction approach such as advanced statistical iterative reconstruction (ASIR) or model-based iterative reconstruction (MBIR), and the like, to reconstruct images of a target volume of the subject 212. In some examples, the image processor unit 210 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of radiation detectors. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT imaging systems, the x-ray source and the detector array are rotated with a gantry about the imaging plane and around the object to be imaged such that an angle at which the radiation beam intersects the object constantly changes. A group of x-ray radiation attenuation measurements, e.g., projection data, from the detector array at one angular position of the gantry is referred to as a "view." A "scan" of the object includes a set of views made at different angular positions, or view angles, during one revolution of the x-ray source and detector about the object. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, x-ray radiographic imaging, positron emission tomography (PET), or single-photon emission CT (SPECT) acquisition, and/or any other modality including modalities yet to be developed as well as combinations thereof in fused embodiments.

The projection data is processed to reconstruct an image that corresponds to one or more two-dimensional slices taken through the object or, in some examples where the projection data includes extended axial coverage, e.g., Z-axis illumination, a three-dimensional image volume of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed axial coverage is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Referring now to FIG. 3, an exemplary system 300 similar to the system 200 of FIG. 2 is depicted. That is, the system 300 may be a CT imaging system. In accordance with aspects of the present disclosure, the system 300 may be configured for imaging a subject 304 (e.g., the subject 212 of FIG. 2). In one embodiment, the system 300 includes the detector array 208 (see FIG. 2). The detector array 208 further includes a plurality of detector elements 302 that together sense the x-ray radiation beams 206 that pass through the subject 304 (such as a patient) to acquire corresponding projection data. Accordingly, in one embodiment, the detector array 208 is fabricated in a multi-slice configuration including the plurality of rows of cells or detector elements 302. In such a configuration, one or more additional rows of the detector elements 302 are arranged in a parallel configuration for acquiring the projection data.

In certain embodiments, the system 300 is configured to traverse different angular positions around the subject 304 for acquiring desired projection data. Accordingly, the gantry 202 and the components mounted thereon may be configured to rotate about a center of rotation 306 for acquiring the projection data, for example, at different energy levels. Alternatively, in embodiments where a projection angle relative to the subject 304 varies as a function of time, the mounted components may be configured to move along a general curve rather than along a segment of a circle.

As the x-ray source 204 and the detector array 208 rotate, the detector array 208 collects data of the attenuated x-ray beams. The data collected by the detector array 208 undergoes pre-processing and calibration to condition the data to represent the line integrals of the attenuation coefficients of the scanned subject 304. The processed data are commonly called projections.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the system 300 reveals internal features of the subject 304, expressed in the densities of two basis materials. The density image, or combinations of multiple density images, may be displayed to show these features. In traditional approaches to diagnosis of medical conditions, such as disease states, and more generally of medical events, a radiologist or physician would consider a hard copy or display of the density image, or combinations thereof, to discern characteristic features of interest. Such features might include lesions, sizes and shapes of particular anatomies or organs, and other features that would be discernable in the image based upon the skill and knowledge of the individual practitioner.

In one embodiment, the system 300 includes a control mechanism 308 to control movement of the components such as rotation of the gantry 202 and the operation of the x-ray source 204. In certain embodiments, the control mechanism 308 further includes an x-ray controller 310 configured to provide power and timing signals to the x-ray source 204. Additionally, the control mechanism 308 includes a gantry motor controller 312 configured to control a rotational speed and/or position of the gantry 202 based on imaging requirements.

In certain embodiments, the control mechanism 308 further includes a data acquisition system (DAS) 314 configured to sample analog data received from the detector elements 302 and convert the analog data to digital signals for subsequent processing. For photon-counting imaging systems, the DAS 314 downloads measured photon counts in one or more energy bins from detector array 208. The DAS 314 may be further configured to selectively aggregate analog data from a subset of the detector elements 302 into so-called macro-detectors, as described further herein. The data sampled and digitized by the DAS 314 is transmitted to a computer or computing device 316. In one example, the computing device 316 stores the data in a storage device or mass storage 318. The storage device 318, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 316 provides commands and parameters to one or more of the DAS 314, the x-ray controller 310, and the gantry motor controller 312 for controlling system operations such as data acquisition and/or processing. In certain embodiments, the computing device 316 controls system operations based on operator input. The computing device 316 receives the operator input, for example, including commands and/or scanning parameters via an operator console 320 operatively coupled to the computing device 316. The operator console 320 may include a keyboard (not shown) or a touchscreen to allow the operator to specify the commands and/or scanning parameters.

Although FIG. 3 illustrates only one operator console 320, more than one operator console may be coupled to the system 300, for example, for inputting or outputting system parameters, requesting examinations, plotting data, and/or viewing images. Further, in certain embodiments, the system 300 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the system 300 either includes, or is coupled to, a picture archiving and communications system (PACS) 324. In an exemplary implementation, the PACS 324 is further coupled to a remote system such as an RIS, EHR/HIS, and/or to an internal or external network (not shown) to allow operators at different locations to supply commands and parameters and/or gain access to the image data.

The computing device 316 uses the operator-supplied and/or system-defined commands and parameters to operate a table motor controller 326, which in turn, may control a table 214 which may be a motorized table. Specifically, the table motor controller 326 may move the table 214 for appropriately positioning the subject 304 in the gantry 202 for acquiring projection data corresponding to the target volume of the subject 304.

As previously noted, the DAS 314 samples and digitizes the projection data acquired by the detector elements 302. Subsequently, an image reconstructor 330 uses the sampled and digitized x-ray data to perform high-speed reconstruction. Although FIG. 3 illustrates the image reconstructor 330 as a separate entity, in certain embodiments, the image reconstructor 330 may form part of the computing device 316. Alternatively, the image reconstructor 330 may be absent from the system 300 and instead the computing device 316 may perform one or more functions of the image reconstructor 330. Moreover, the image reconstructor 330 may be located locally or remotely, and may be operatively connected to the system 300 using a wired or wireless network. For example, one embodiment may use computing resources in a cloud network cluster for the image reconstructor 330.

In one embodiment, the image reconstructor 330 stores the images reconstructed in the storage device 318, either via the computing device 316 as shown in FIG. 3 or via a direct connection (not shown). Alternatively, the image reconstructor 330 may transmit the reconstructed images to the computing device 316 for generating useful patient information for diagnosis and evaluation. In certain embodiments, the computing device 316 may transmit the reconstructed images and/or the patient information to a display or display device 332 communicatively coupled to the computing device 316 and/or the image reconstructor 330. In some embodiments, the reconstructed images may be transmitted from the computing device 316 or the image reconstructor 330 to the storage device 318 for short-term or long-term storage.

Some methods or processes described further herein may be stored as executable instructions in non-transitory memory on a computing device (or controller) in system 300. In one embodiment, image reconstructor 330 may include such executable instructions in non-transitory memory, and may apply the methods described herein to reconstruct an image from scanning data. In another embodiment, computing device 316 may include the instructions in non-transitory memory, and may apply the methods described herein, at least in part, to a reconstructed image after receiving the reconstructed image from image reconstructor 330. In yet another embodiment, the methods and processes described herein may be distributed across image reconstructor 330 and computing device 316.

In one embodiment, the display device 332 allows the operator to evaluate the imaged anatomy. The display device 332 may also allow the operator to select a volume of interest (VOI) and/or request patient information, for example, via a graphical user interface (GUI) for a subsequent scan or processing.

The computing device 316 may further store an intelligent automated protocoling system 334 thereon, which may interface with various components of the system 300 via an interface 335. Accordingly, the intelligent automated protocoling system 334 may receive medical data from the PACS 324 or from a remote device storing another IT system (e.g., a CDS, EHR/HIS, RIS, VNA, MPI, etc.) and protocols from a master protocol library (not shown at FIG. 3), whereby the intelligent automated protocoling system 334 may automatically generate one or more protocol recommendations. A scan protocol may then be automatically selected from the one or more protocol recommendations, which may further be confirmed by an operator at the operator console 320. In some examples, the operator may instead enter a manual selection from the one or more protocol recommendations into the operator console 320 or may manually select another scan protocol entirely (e.g., not included in the one or more protocol recommendations). The intelligent automated protocoling system 334 may further interface (e.g., via the interface 335) to a recommendation model that may be periodically updated with feedback from the operator via the intelligent automated protocoling system 334 such that scan protocols may be more consistently recommended via adaptive learning paradigms.

It will be appreciated that the intelligent automated protocoling system 334 may be substantially similar to the intelligent automated protocoling system 104 of FIG. 1, excepting that the intelligent automated protocoling system 334 is specifically adapted to a single imaging modality (that is, CT imaging). However, it will be further appreciated that non-modality specific functionality of the intelligent automated protocoling system 334 may be substantially equivalent to that described above with reference to the protocoling recommendation system 104. Accordingly, further non-modality specific components of FIG. 1 may be added or substituted to the system 300 within the scope of the present disclosure.

As explained previously, protocoling encompasses the entire journey of mapping the order level protocol (procedure requested by the physician) to the radiologist level protocol and then eventually to the scanner level protocol. The whole process can be split into two phases—mapping the order level protocol to radiologist level protocol, performed by a radiologist, and choosing/selecting the scan level protocol based on the radiologist level protocol, performed by a technologist. Since the two phases are performed manually by two different professionals, certain issues/problems may arise at the protocoling stage. These issues may include undue time expenditure for both the radiologist and technologist in selecting the proper protocol and image quality, dose issues, and/or patient recall if an improper protocol is selected.

To address the above-described pain points, a protocol recommendation system may be implemented that uses an optimization engine to auto-generate protocol recommendations for a given imaging order. The architecture leverages patient demographic information and the historically encountered pattern of protocol selection to predict an accurate and reliable protocol suggestion.

The architecture may include an interface layer (which may be a REST API based interface layer) that acts as the interface for a recommendation model and the processing layer for any external client interactions. The layer creates a REST API based wrapper around the core optimization system enabling the capability to train or infer from the core optimization system. The processing layer is responsible for ingesting the incoming training or inferencing request received from the interface layer, processing as per the workflow, fetching or saving necessary information from the database, and invoking the recommendation model in case of recommendation requests.

Thus, the optimization engine/recommendation system disclosed herein may store and persist historical selections data along with associated patient demographic data and predict and recommend a scan level protocol for an imaging order based on the historical selection and patient demographic data.

To facilitate this, an agent (e.g., a scanner, such as scanner 108) may communicate with a core (e.g., the server 102 of FIG. 1), to synchronize data between the agent and core (e.g., the historical selections data and recommended scan protocols). Data synchronization across two systems has been a common challenge in data storage and management. For a modality equipment to keep syncing its database with another equipment or edge device (e.g., for the scanner to sync its database with the server), it becomes even more challenging due various factors. For example, the standard available data synchronization between the core and agent requires additional/specific protocols like (PPTP, SSTP) to be established between the devices. The systems require to have a persistent connection established and maintained between the two systems. Constrained and varied security restraints are imposed on the participating systems. Inefficient synchronizing algorithms may be used that require large payload exchange for identification of mismatched data, resulting in unnecessary exchange of large volumes of data across the systems. The process of synchronizing data and maintaining connection requires intensive resource utilization. The failover management for data synchronization is not efficient and robust, and it may require some form of manual intervention to complete the process of synchronization.

To address the above pain points, a custom protocol layered over the traditional REST APIs is presented herein to enable a core and agent interaction that can synchronize the data across the modality systems. The architecture leverages REST principles and implementation to achieve a robust data synchronization. As described herein, automatic data synchronization across modality equipment using REST interfaces may be performed, including automatically identifying mismatched data blocks and reducing data exchanged with individual API payload. An example system architecture for this process is shown in FIG. 4.

FIG. 4 schematically shows a data synchronization system 400 including a core 402 and an agent 404. The core 402 is a non-limiting example of server 102 of FIG. 1 and the agent 404 is a non-limiting example of a scanner 108. When the agent 404 is a CT imaging system, the agent 404 may be part of the computing device 316. The core 402 may include or be operably coupled to a database 410 on which information usable to recommend protocols may be stored. For example, the database 410 may store procedure-to-protocol mappings whereby scan protocols performed in prior scans are mapped to procedures or procedure groups. The database 410 may further store patient demographic data (e.g., age, sex, body mass index) for each prior scan. The database 410 may interact with a fingerprint management and data access layer 412. Via a REST interface 414, the core 402 may communicate with the agent 404.

The agent 404 may likewise include a database 420 where, for each scan performed via the scanner including the agent 404, scan protocols executed for the scan and patient demographic data for the patient scanned may be stored. To synchronize the data stored in database 420 with the data stored in database 410, the agent 404 may include a fingerprint management and data access layer 416.

As shown in FIG. 4, various types of information may be communicated between the agent 404 and the core 402, including block identification information, mismatch data and fingerprint information, and mismatch record information. Additional information about the data synchronization using the system 400 is described below with respect to FIGS. 5-11.

In this way, a complete data synchronization process is built as the custom protocol over the standard REST paradigm and requires only REST interactions to be enabled for data synchronization. The API implementation of the "Sync Protocol" is stateless in nature and does not require long persistent connections to be established and maintained. The configuration disclosed herein uses the scheme of fingerprints of fingerprints (referred as FOF) for identifying mismatched blocks, which reduces the overall time taken by the synchronization as well as reduces the payload size, improving the efficiency and making the configuration an optimal candidate for performing synchronizations over a slow network. The pure REST implementation of the "Sync Protocol" is not constrained for a specific database and can be implemented to support two systems operating with different types of databases. The REST implementation with HTTPS uses TCP protocol under the hood, which minimizes the need for establishing additional handshake or protocol management and allows efficient data synchronization through one or more firewalls and/or via a cloud-based system. The API implementation is stateless which also eliminates the need to open any sockets and adds robustness to the data sync process, a single failure for a request response pair of any of the APIs within a specific sync cycle (due to network disruptions) would not affect subsequent synchronization cycles.

The workflow may include repeating cycles of data synchronization identified as "Sync Protocol" at periodic intervals to synchronize data across the systems. Each sync protocol may include three distinct REST API-based interactions between the agent and the core in order to identify the data to be synced and synchronize the mismatched data, which is shown by the high-level flow chart of FIG. 5, which illustrates a method 500 for data synchronization. Method 500 is carried out by both an agent and a core, such as the computing device 316 and the server 102, according to instructions stored in non-transitory memory of each of the agent and the core.

At 502, method 500 includes performing block identification. The first interaction of the data synchronization includes the agent initiating the interaction with the core and requesting for the identification of the block for synchronization, which is explained in more detail below with respect to FIGS. 6 and 7 (from the perspective of the agent and the core, respectively). At the end of a successful interaction with the core, the agent receives the block number which uniquely identifies the block which the core would prefer to sync. At 504, method 500 includes performing fingerprinting and data sharing. The second interaction includes the agent sharing the fingerprint list of the records available in the agent database for the identified block to the core and initiating the interaction to identify the data mismatch between agent and core, which is explained in more detail below with respect to FIGS. 8 and 9 (from the perspective of the agent and the core, respectively). At the end of the step, the agent receives a list of records/data points that the core has identified as new data that needs to be stored on agent. The agent creates a fingerprint for each of these records using a SHA-256 encryption of the data and stores the data along with the fingerprints for future sync cycles. It also receives a list of fingerprints that the core has identified as the mismatched data that the core is missing and would need it to be shared by the agent. The agent leverages this information in the next step to initiate saving records on the core. At 506, method 500 includes performing records sharing. The third interaction includes the agent creating a payload of associated data for the identified fingerprints from the second interaction and starting the interaction for storing data on the core, as explained in more detail below with respect to FIGS. 10 and 11 (from the perspective of the agent and the core, respectively). At the end of successful interaction for storing records, the core indicates the same to the agent via success message as response. The saving of records on the core marks the completion of one "Sync Protocol" cycle.

Figure 5:
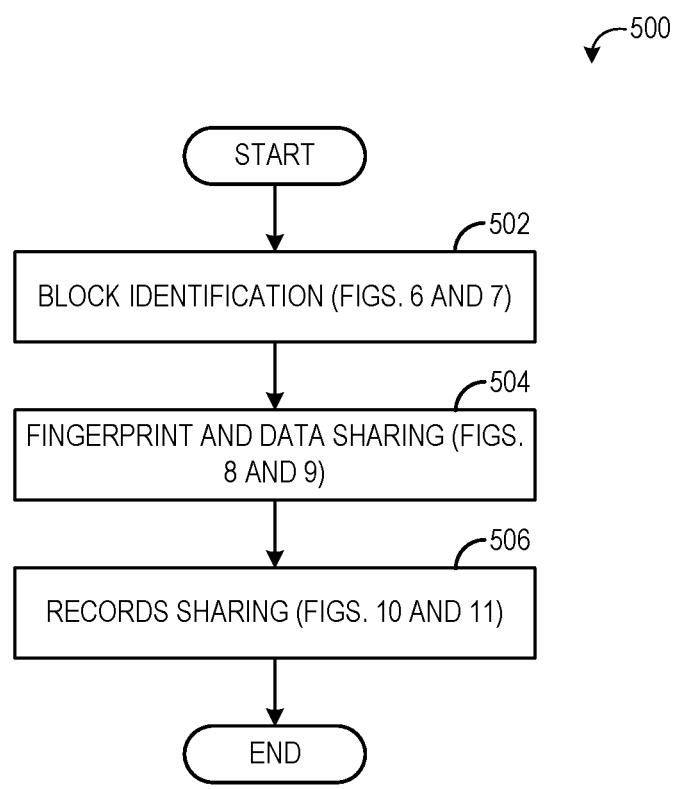
FIG. 5 is a flow chart illustrating an example high-level method for data synchronization between an agent and a core.

While FIG. 5 illustrates the three interactions between the core and the agent for syncing data on the core database with data on the agent database, it is to be appreciated that the core may be communicatively coupled to a plurality of agents, and the core database may be populated with data from each agent. During a given synchronization event with a selected agent, data records on the core database received from other agents are shared with the selected agent. In this way, data from each agent database may be shared with the core database, which may then in turn share all the data with each agent, thereby ensuring each agent receives data records from each other agent.

Figure 6:
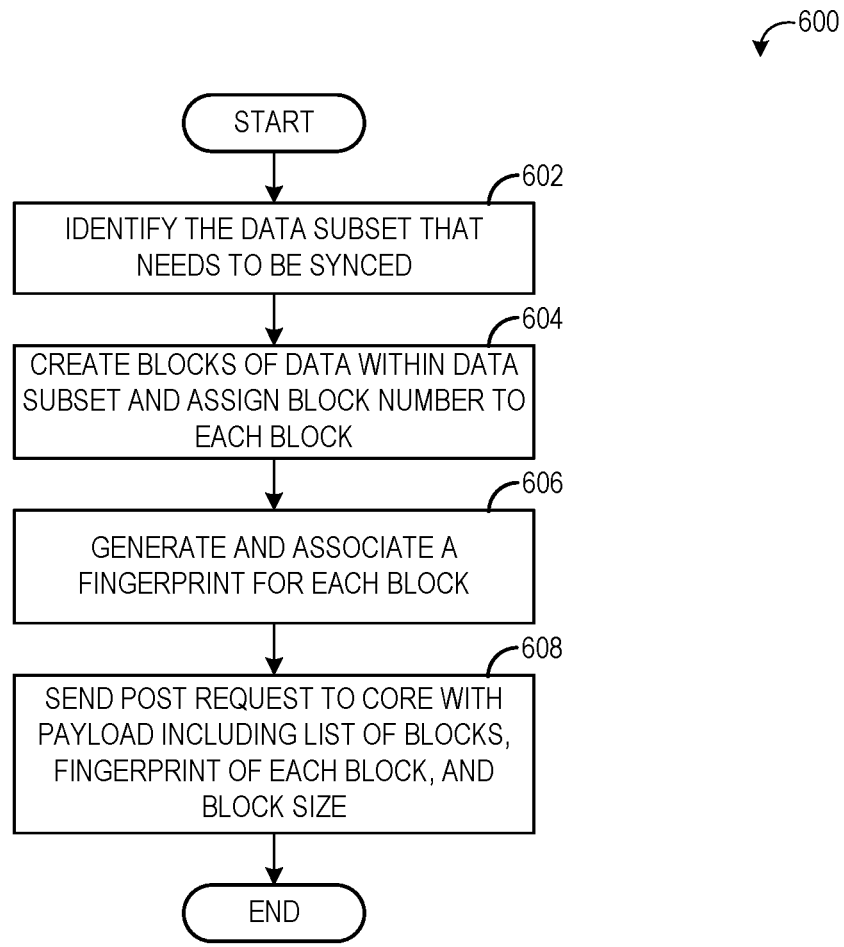
FIGS. 6 and 7 are flow charts illustrating an example method for data block identification, from the perspective of an agent and a core, respectively.

FIG. 6 is a flow chart illustrating a method 600 for block identification from the perspective of the agent. Thus, method 600 is carried out according to non-transitory instructions stored in memory of the agent, such as instructions stored in memory of computing device 316. Briefly, the block identification includes identification by the agent of a data subset that the agent would like to sync, which may be a configurable parameter determined by the agent derived from the use case. The process of block identification provides the block that needs to be synced, and initially the agent is unaware of what needs to be synced and hence the agent creates fingerprints of all blocks within the desired subset and shares the fingerprints with the core. In response, as explained in more detail below with respect to FIG. 7, the core verifies and matches these fingerprints with the blocks present on the core and identifies the mismatched/missing fingerprints, which helps in identification of which block needs to be synced.

At 602, the data subset that is to be synced is identified. The data subset that is to be synced may be identified based on that data subset being saved in the database of the agent since a prior data synchronization was performed, or based on another suitable mechanism for identifying the data subset. The data subset may include records saved in the database of the agent, such as executed scan protocols and patient demographic information. At 604, blocks of data are created within the data subset and a block number is assigned to each block. For example, the agent creates blocks of data within the identified data subset based on a predetermined/agreed upon unique identifier column and assigns a block number to each of the data blocks. The data may be partitioned into the data blocks based on date ranges. For example, the data may be partitioned into blocks each including seven days of data records, such that a first data block may include all records over a first seven-day period, a second data block may include all records over a seven-day period immediately prior to the first seven-day period, etc.

At 606, a fingerprint is generated for and associated with each block. The fingerprints are generated using the fingerprint values of the individual records available in the block. Thus, each data block may be assigned a fingerprint based on the fingerprints of each record in that data block, which may be referred to as a fingerprint of fingerprints (FOF). At 608, a POST request is sent to the core with a payload that includes a list of the data blocks (e.g., a list of the block numbers), the fingerprint of each data block, and the block size of each data block. For example, the agent makes the POST request to a first endpoint of the core, such as a "/blocks" endpoint of the core. Method 600 then ends.

Figure 7:
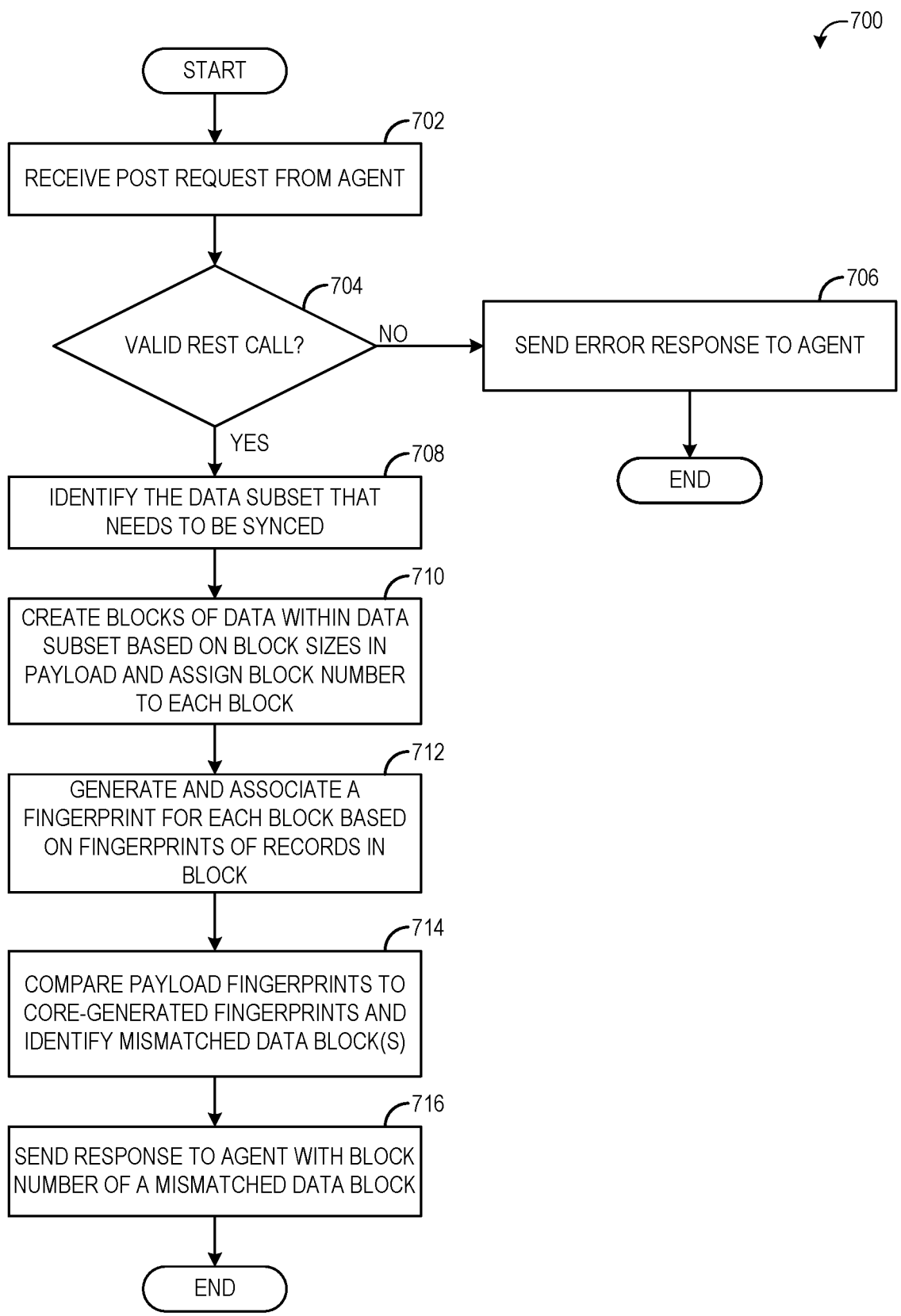

FIG. 7 is a flow chart illustrating a method 700 for block identification from the perspective of the core. Thus, method 700 is carried out according to non-transitory instructions stored in memory of the core, such as instructions stored in memory of server 102. At 702, a POST request is received from the agent. The POST request may be the POST request sent at 608 of method 600, and thus may include a list of data blocks, a fingerprint for each data block, and the block size of each data block. At 704, method 700 determines if the POST request is a valid REST call. If the POST request is not a valid REST call, method 700 proceeds to 706 to send an error response to the agent, and then method 700 ends.

If the POST request is determined to be a valid REST call, method 700 proceeds to 708 to identify the data subset that is to be synced based on the information in the post request payload, such as the list of data blocks. For example, the list of data blocks may identify that the data subset for synchronization includes 28 days of data records partitioned into four blocks, each of a given size and each having a fingerprint. At 710, blocks of data within an equivalent data subset of the database of the core are created based on the block sizes in the received payload, and a block number is assigned to each data block of the core. For example, the core creates blocks of data within the identified data subset of the database of the core, using the block size shared in the payload and based on the predetermined/agreed upon unique identified column, and assigns a block number to each of the data blocks. The core may identify all data records over the time range identified by the list of data blocks sent by the agent (e.g., the prior 28 days) and create its own data blocks from the records in the database of the core, that are then given a block number. At 712, a fingerprint is generated for and associated with each data block of the core based on the fingerprint value of each individual record available in the block. For example, the core may generate a fingerprint for each of the data blocks of the core using the fingerprint values of the individual records available in the block. At 714, the fingerprints in the payload are compared to the fingerprints generated by the core (e.g., at 712) and any blocks for which the fingerprints do not match (e.g., mismatched data blocks) are identified, reflecting a mismatch of data available at the core and agent. At 716, a response is sent to the agent with the block number of one mismatched data block. For example, the core may select one block at random for which the data mismatch is identified and share the associated block number as the response to the REST call. If all the fingerprints match, then the core may assume that no data is missing from the core database and a response is sent indicating that data synchronization is not needed. Method 700 then ends. By identifying one mismatched block, the core may enable syncing of only one block of data at a time, which may allow syncing on slow and/or limited networks. Further, the stateless nature of the syncing protocol is more feasible and easier to implement when only one block is tracked and managed at a time.

Figure 8:
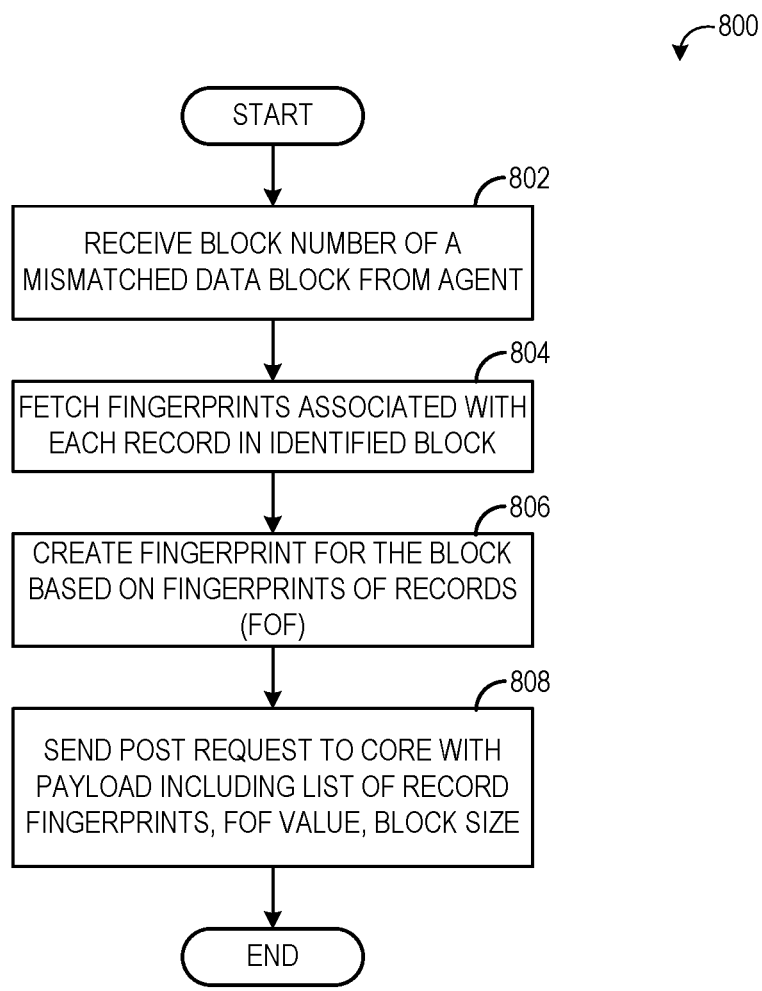
FIGS. 8 and 9 are flow charts illustrating an example method for fingerprinting and data sharing, from the perspective of an agent and a core, respectively.

FIG. 8 is a flow chart illustrating a method 800 for fingerprint and data sharing from the perspective of the agent. Thus, method 800 is carried out according to non-transitory instructions stored in memory of the agent, such as instructions stored in memory of computing device 316. At 802, a block number of a mismatched data block is received from the core, e.g., via the response sent at 716 of method 700. At 804, fingerprints associated with each record in the identified block are fetched. At 806, a fingerprint for the block is created based on the fingerprints of the records available in the block, e.g., the fingerprint of the fingerprints (FOF). The fingerprinting may be performed using hashing, such as SHA-256 encryption. The FOF generated at 806 may not be directly leveraged by the core but is generated/used to keep consistency across different REST calls. At 808, a POST request is sent to the core with a payload including a list of record fingerprints, a value for the FOF (FOF value), and the block size used for creating the blocks. The POST request may be sent to a second endpoint of the core, such as a "/blocks/blockID/fingerprintQueries" endpoint of the core. Method 800 then ends.

Figure 9:
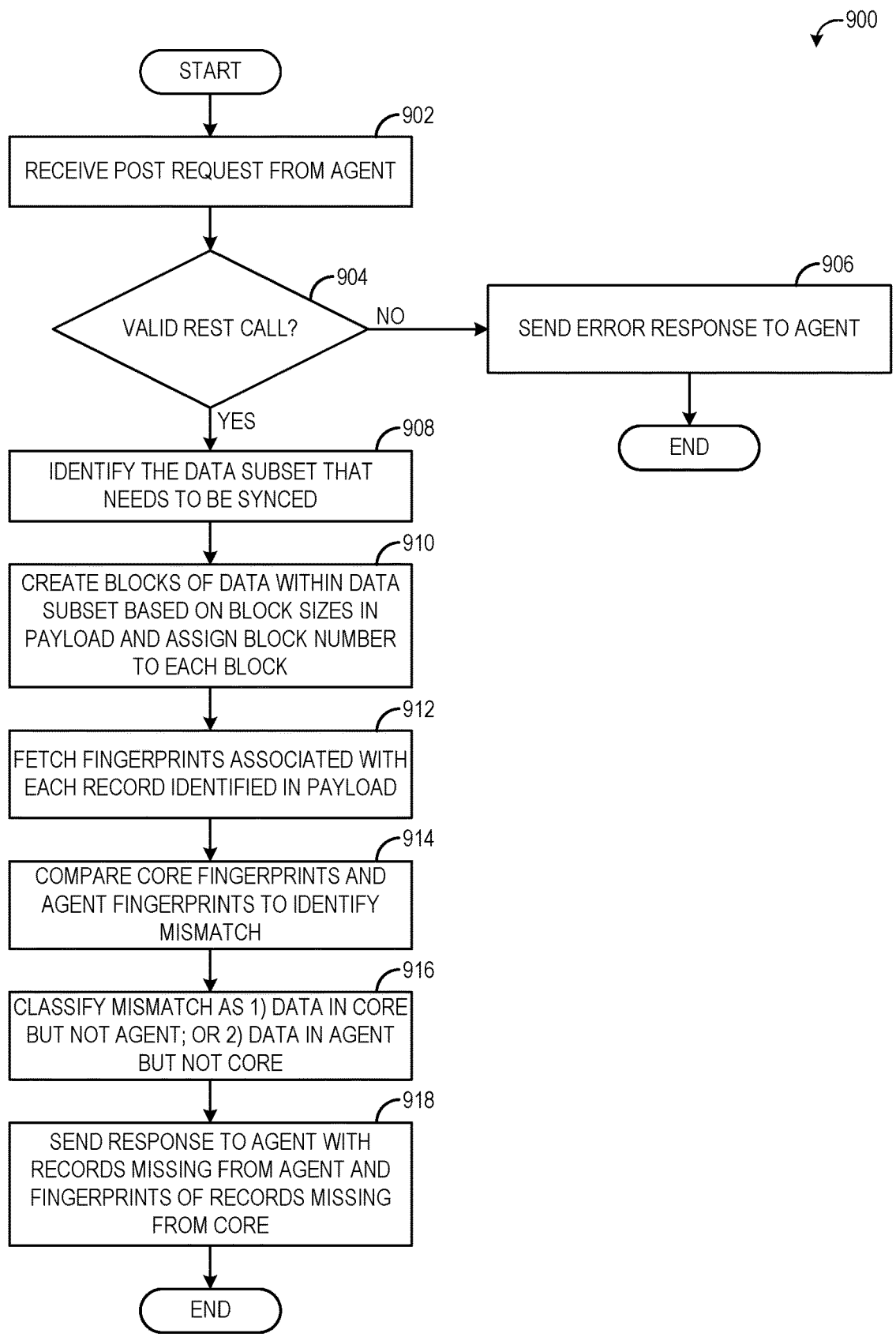

FIG. 9 is a flow chart illustrating a method 900 for fingerprint and data sharing from the perspective of the core. Thus, method 900 is carried out according to non-transitory instructions stored in memory of the core, such as instructions stored in memory of server 102. At 902, a POST request is received from the agent. The POST request may be the POST request sent at 808 of method 800, and thus may include a list of record fingerprints, a FOF value, and the block size used for creating the blocks. At 904, method 900 determines if the POST request is a valid REST call. If the POST request is not a valid REST call, method 900 proceeds to 906 to send an error response to the agent, and then method 900 ends.

If the POST request is determined to be a valid REST call, method 900 proceeds to 908 to identify the data subset that is to be synced (e.g., based on the information sent by the agent). At 910, data blocks within the data subset (on the core database) are created based on the block size from the payload and a block number is assigned to each data block. At 912, fingerprints associated with each record (e.g., stored on the core database) identified in the payload are fetched, and at 914, the core fingerprints are compared to the agent fingerprints to identify a mismatch in the records. At 916, each mismatch is identified as belonging to one of two categories: 1) the data record(s) are stored on the core database but not the agent database; or 2) the data record(s) are stored on the agent database but not the core database. At 918, the core sends a response to the agent with the records that are missing from the agent and with the fingerprints of the records on the agent database that are missing from the core database. Method 900 then ends.

Figure 10:
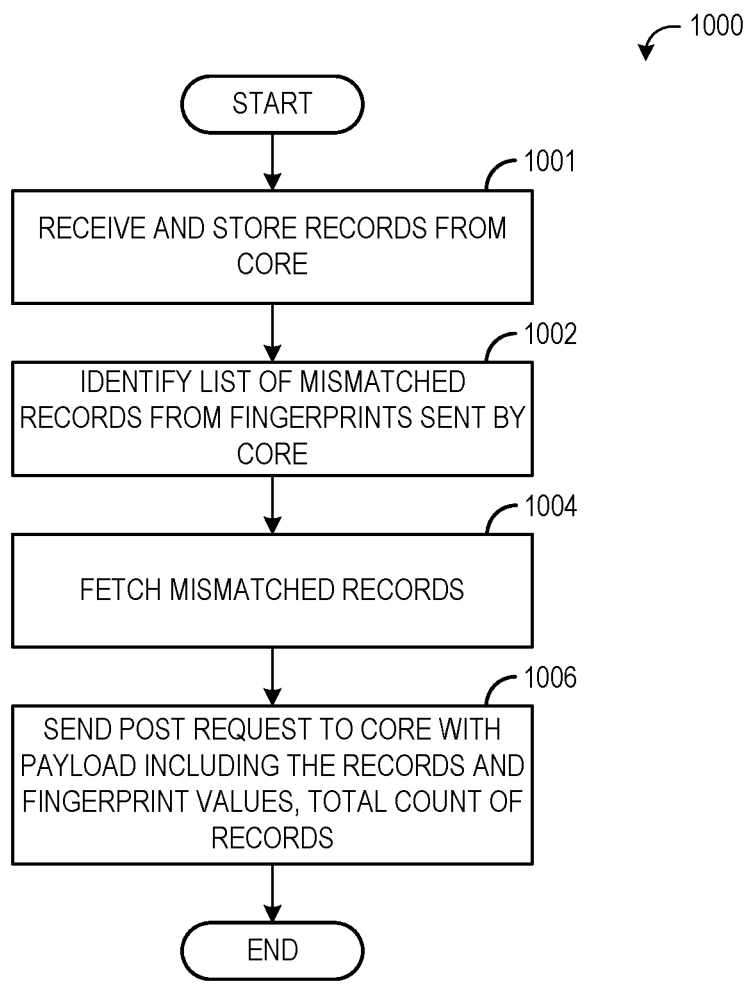
FIGS. 10 and 11 are flow charts illustrating an example method for record sharing, from the perspective of an agent and a core, respectively.

FIG. 10 is a flow chart illustrating a method 1000 for record sharing from the perspective of the agent. Thus, method 1000 is carried out according to non-transitory instructions stored in memory of the agent, such as instructions stored in memory of computing device 316. At 1001, the records sent by the core (e.g., in the response sent at 918 of method 900) are received and stored in the agent database. At 1002, a list of mismatched records is identified from the fingerprints sent by the core. For example, as explained above with respect to FIG. 9, the core may send a response to the agent that includes the fingerprints of the records stored on the agent database that are missing from the core database. At 1004, the agent fetches the records corresponding to the fingerprints sent by the core (e.g., the mismatched records). At 1006, a POST request is sent by the agent to the core with a payload that includes the records and fingerprint values, and a total count of the records. For example, the POST request may be sent to a third endpoint of the core (e.g., a "/records" endpoint), with the request payload including the data/records along with the respective fingerprint values for each record and a total count of the records being shared. Method 1000 then ends.

Figure 11:
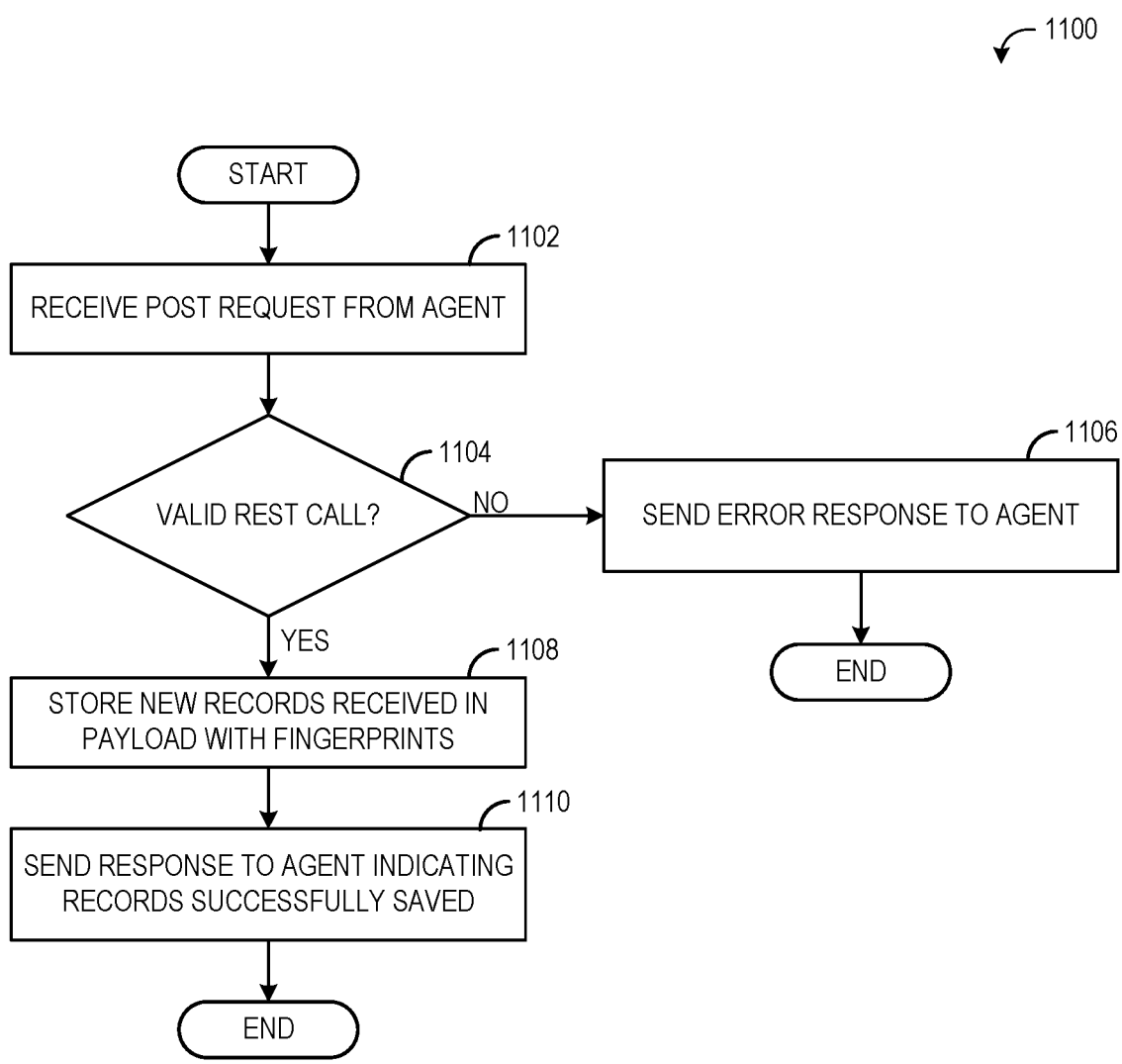

FIG. 11 is a flow chart illustrating a method 1100 for record sharing from the perspective of the core. Thus, method 1100 is carried out according to non-transitory instructions stored in memory of the core, such as instructions stored in memory of server 102. At 1102, a POST request is received from the agent. The POST request may be the POST request sent at 1006 of method 1000, and thus may include the records requested by the core, the fingerprint values of the records, and a total count of the records. At 1104, method 1100 determines if the POST request is a valid REST call. If the POST request is not a valid REST call, method 1100 proceeds to 1106 to send an error response to the agent, and then method 1100 ends.

If the POST request is determined to be a valid REST call, method 1100 proceeds to 1108 to store the new records received in the payload of the POST request along with the fingerprints of the records in the core database. At 1110, a response is sent to the agent indicating that the records were successfully saved. Method 1100 then ends.

Thus, the data synchronization process disclosed herein provides many benefits. For example, the data synchronization process is built as the custom protocol over the standard REST interface and requires only REST interactions to be enabled. The API implementation of the sync protocol is stateless in nature and does not require long persistent connections to be established and maintained. The Sync Protocol uses REST paradigm for data exchange, which can be implemented in multiple tech stacks ensuring that the data exchange protocol supports cross platform implementation. The proposed design uses the scheme of fingerprints of fingerprints (referred as FOF) for identifying mismatched blocks which reduces the overall time taken by the synchronization as well as reduces the payload size, improving the efficiency and enabling synchronizations over a slow network. The pure REST implementation of the Sync Protocol is not constrained for a specific database and can easily be implemented to support two systems operating on different databases. The API implementation is stateless which also adds robustness to the data sync process, as a single failure for a request response pair of any APIs within a specific sync cycle due to network disruptions would not affect subsequent synchronization cycles. The REST implementation using HTTPS uses TCP protocol under the hood, minimizing need for establishing additional handshake or protocol management. The REST API implementation has added the ability to define the size of blocks as part of the request payload which adds the flexibility to select the data size to be synced in each sync cycle resulting in finer control on payload exchange size and network load. For example, the client system (e.g., agent) may vary the size of data exchanged in a single "Sync" cycle by simply changing the block size, since the parameter is part of the REST interface, the server (e.g., core) will account for the change. Thus, in some examples an adaptive mechanism may be used to vary block size based on network availability or other parameters. The proposed REST implementation can be extended and scaled to act as a data aggregator and distributor by adding multiple agents to interact with the same core, resulting in data aggregation and exchange across agents.

The disclosed synchronization protocol can be leveraged for automatic data exchange between a modality equipment (e.g., a CT imaging system) and an edge server, minimizing human intervention and support needed from an on-field staff member. Further, the disclosed synchronization protocol supports cross platform implementation which can be leveraged to establish data exchange across different modality systems without restriction of the platform or the environment, improving cross modality interaction and data exchange.

The disclosed synchronization protocol can also be extended to operate as a data aggregator and data distributor platform, across modality equipment. Multiple agents can interact and synchronize with a single core in which case the core behaves as the data aggregator and distributor. The disclosed synchronization protocol can perform very well for synchronizations over a slow network, making the protocol an ideal choice for synchronizing systems with constrained network bandwidth saving the overall cost and time.

A technical effect of automatically synchronizing data stored on a core database with data stored on one or more agent databases using a REST interface is that data may be synchronized without long persistent connections being established and maintained, thereby facilitating synchronization over slow networks. Another technical effect is that the disclosed data synchronization protocol supports cross-platform implementation, reduces payload size, reduces the number of handshakes needed, and can be extended and scaled to facilitate data aggregation and distribution.

In another representation, a method for synchronizing data between an agent and a core includes, receiving, at the core, a request from the agent identifying a data subset of the agent to be synchronized, the request further including a fingerprint for each block of data in the data subset; sending, from the core, a response to the agent identifying a block of mismatched data between the core and the agent, the block of mismatched data identified based on comparing each fingerprint in the request to fingerprints of corresponding data blocks of the core; receiving, at the core, a request from the agent identifying a list of fingerprints of data records of the block of mismatched data stored at the agent; identifying, with the core, mismatched data records based on the list of fingerprints; for mismatched data records that are stored at the core, fetching the mismatched data records; sending, from the core, a response to the agent including the fetched mismatched data records and a list of fingerprints of mismatched data records stored at the agent; and receiving, from the agent, one or more data records identified by the list of fingerprints of the mismatched data records.

In another representation, a method for synchronizing data between an agent and a core includes receiving, at the core, a request from the agent identifying a data subset of the agent to be synchronized, the request further including a fingerprint for each block of data in the data subset; identifying, with the core, a corresponding data subset of the core; generating, with the core, a fingerprint for each block of the corresponding data subset; comparing, with the core, each fingerprint in the request to each fingerprint of the corresponding data subset; sending, from the core, a response to the agent identifying a block of mismatched data between the core and the agent, the block of mismatched data identified based on the comparing; fetching, with the agent, a fingerprint for each record of the identified block of mismatched data and creating a fingerprint of the block based on the fetched fingerprints; sending, from the agent, a request to the core including the fingerprint of the block; and receiving, at the agent, one or more records from the core identified via the fingerprint of the block.

The disclosure also provides support for a method for synchronizing data between an agent and a core, comprising: sending, from the agent, a request to the core identifying a data subset to be synchronized, the request further including a fingerprint for each block of data in the data subset, receiving, at the agent, a response from the core identifying a block of mismatched data between the core and the agent, the block of mismatched data identified based on the fingerprint for that block, fetching, with the agent, a fingerprint for each record of the identified block of mismatched data and creating a fingerprint of the block based on the fetched fingerprints, sending, from the agent, a request to the core including the fingerprint of the block, and receiving, at the agent, one or more records from the core identified via a comparison of fingerprints of the one or more records. In a first example of the method, each request sent from the agent to the core is a POST request. In a second example of the method, optionally including the first example, the agent comprises a computing device of a medical imaging system and includes or is operatively coupled to an agent database storing records pertaining to patient scans performed with the medical imaging system. In a third example of the method, optionally including one or both of the first and second examples, the core comprises a central server system including a core database and a recommendation model trained to recommend scan protocols based on one or more records stored in the core database. In a fourth example of the method, optionally including one or more or each of the first through third examples, the method further comprises: storing the one or more records received from the core in an agent database. In a fifth example of the method, optionally including one or more or each of the first through fourth examples, the method further comprises: partitioning the data subset into a plurality of blocks of data, each block of data having a block size determined based on a preselected date range. In a sixth example of the method, optionally including one or more or each of the first through fifth examples, the method further comprises: partitioning the data subset into a plurality of blocks of data, each block of data having a block size dynamically determined based on traffic on a network over which the agent and core communicate. In a seventh example of the method, optionally including one or more or each of the first through sixth examples, the method further comprises: receiving, at the agent, one or more fingerprints each corresponding to a respective record of the agent identified by the core via the fingerprints of the respective records, and sending each respective record to the core.

The disclosure also provides support for a system, comprising: a medical imaging modality configured to perform scans of patients to obtain medical images of the patients, a medical database storing a plurality of records relating to the scans, a processor, and instructions stored in non-transitory memory executable by the processor to: send a request to a core system requesting for identification of a block of data for synchronization, wherein the core system includes a core database, receive, from the core system, a block number identifying the block of data, send, to the core system, a first list of fingerprints of records stored in the medical database, the first list of fingerprints identified based on the block number, receive, from the core system, one or more records stored on the core database and a second list of fingerprints of records stored on the medical database, and send, to the core system, each record stored on the medical database identified by the second list of fingerprints. In a first example of the system, the instructions are further executable to receive a recommended scan protocol for a selected patient scan from the core system. In a second example of the system, optionally including the first example, the requests sent to the core system include POST requests sent over a REST interface. In a third example of the system, optionally including one or both of the first and second examples, the instructions are further executable to save, at the medical database, the one or more records received from the core system. In a fourth example of the system, optionally including one or more or each of the first through third examples, the core system is in communication with a plurality of additional medical databases, each additional medical database associated with a respective medical imaging modality, and wherein at least one of the one or more records received from the core system originated at one of the additional medical databases. In a fifth example of the system, optionally including one or more or each of the first through fourth examples, the medical imaging modality is a computed tomography scanner.

The disclosure also provides support for a system, comprising: a core system including a core database, a plurality of medical imaging systems each in communication with the core system and each including a respective medical database, wherein the core system stores instructions in non-transitory memory that are executable by a processor to: automatically synchronize data stored on the core database with data stored on each medical database using a REST interface, including identifying data stored on the core database that is to be shared with a first medical database based on a fingerprint of fingerprints of data stored on the first medical database. In a first example of the system, identifying data stored on the core database that is to be shared with the first medical database based on the fingerprint of fingerprints of data stored on the first medical database comprises: receiving the fingerprint of fingerprints from a first medical imaging system including the first medical database via the REST interface, comparing the fingerprint of fingerprints to a core-generated fingerprint of fingerprints, determining that the core-generated fingerprint of fingerprints does not match the fingerprint of fingerprints, and in response, sending a response to the first medical imaging system, via the REST interface, identifying a block number to be synced. In a second example of the system, optionally including the first example, the instructions are further executable to receive a response from the first medical imaging system, via the REST interface, including a list of record fingerprints for individual records within a block of data of the first medical database identified by the block number, compare the list of record fingerprints to a core-generated list of record fingerprints for individual records within a block of data of the core database identified by the block number, and send a response to the first medical imaging system, via the REST interface, including any records of the block of data of the core database missing from the first medical database and fingerprints of any records of the block of data of the first medical database missing from the core database, identified via the comparing. In a third example of the system, optionally including one or both of the first and second examples, automatically synchronizing data stored on the core database with data stored on each medical database using the REST interface comprises receiving data from the first medical database and pushing the data from the first medical database to each remaining medical database using the REST interface. In a fourth example of the system, optionally including one or more or each of the first through third examples, the instructions are executable to automatically synchronize only a single block of data with a selected medical database at a time. In a fifth example of the system, optionally including one or more or each of the first through fourth examples, the plurality of medical imaging systems comprises a plurality of computed tomography scanners.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for synchronizing data between an agent and a core, comprising:
    sending, from the agent, a first request to the core identifying a data subset to be synchronized, the first request further including a fingerprint for each block of data in the data subset;
    receiving, at the agent, a response from the core identifying a block of mismatched data between the core and the agent, the block of mismatched data identified based on the fingerprint for that block;
    fetching, with the agent, a fingerprint for each record of the identified block of mismatched data and creating a fingerprint of the block based on the fetched fingerprints;
    sending, from the agent, a second request to the core including the fingerprint of the block; and
    receiving, at the agent, one or more records from the core identified via a comparison of fingerprints of the one or more records.

2. The method of claim 1, wherein each of the first request and the second request sent from the agent to the core is a POST request.

3. The method of claim 1, wherein the agent comprises a computing device of a medical imaging system and includes or is operatively coupled to an agent database storing records pertaining to patient scans performed with the medical imaging system.

4. The method of claim 3, wherein the core comprises a central server system including a core database and a recommendation model trained to recommend scan protocols based on one or more records stored in the core database.

5. The method of claim 1, further comprising storing the one or more records received from the core in an agent database.

6. The method of claim 1, further comprising partitioning the data subset into a plurality of blocks of data, each block of data having a block size determined based on a preselected date range.

7. The method of claim 1, further comprising partitioning the data subset into a plurality of blocks of data, each block of data having a block size dynamically determined based on traffic on a network over which the agent and core communicate.

8. The method of claim 1, further comprising receiving, at the agent, one or more fingerprints each corresponding to a respective record of the agent identified by the core via the fingerprints of the respective records, and sending each respective record to the core.

9. A system, comprising:
    a medical imaging modality configured to perform scans of patients to obtain medical images of the patients;

a medical database storing a plurality of records relating to the scans;

a processor; and instructions stored in non-transitory memory executable by the processor to:
  send a request to a core system requesting for identification of a block of data for synchronization, wherein the core system includes a core database;
  receive, from the core system, a block number identifying the block of data;
  send, to the core system, a first list of fingerprints of records stored in the medical database, the first list of fingerprints identified based on the block number;
  receive, from the core system, one or more records stored on the core database and a second list of fingerprints of records stored on the medical database; and
  send, to the core system, each record stored on the medical database identified by the second list of fingerprints.

10. The system of claim 9, wherein the instructions are further executable to receive a recommended scan protocol for a selected patient scan from the core system.

11. The system of claim 9, wherein the requests sent to the core system include POST requests sent over a REST interface.

12. The system of claim 9, wherein the instructions are further executable to save, at the medical database, the one or more records received from the core system.

13. The system of claim 9, wherein the core system is in communication with a plurality of additional medical databases, each additional medical database associated with a respective medical imaging modality, and wherein at least one of the one or more records received from the core system originated at one of the additional medical databases.

14. The system of claim 9, wherein the medical imaging modality is a computed tomography scanner.

15. A system, comprising:
  a core system including a core database;
  a plurality of medical imaging systems each in communication with the core system and each including a respective medical database, wherein the core system stores instructions in non-transitory memory that are executable by a processor to:
    automatically synchronize data stored on the core database with data stored on each medical database using a REST interface, including identifying at least a portion of the data stored on the core database that is to be shared with a first medical database based on a fingerprint of fingerprints of data stored on the first medical database.

16. The system of claim 15, wherein identifying the at least the portion of the data stored on the core database that is to be shared with the first medical database based on the fingerprint of fingerprints of data stored on the first medical database comprises:
  receiving the fingerprint of fingerprints from a first medical imaging system including the first medical database via the REST interface;
  comparing the fingerprint of fingerprints to a core-generated fingerprint of fingerprints; and
  determining that the core-generated fingerprint of fingerprints does not match the fingerprint of fingerprints, and in response, sending a response to the first medical imaging system, via the REST interface, identifying a block number to be synced.

17. The system of claim 16, wherein the instructions are further executable to receive a response from the first medical imaging system, via the REST interface, including a list of record fingerprints for individual records within a block of data of the first medical database identified by the block number;
  compare the list of record fingerprints to a core-generated list of record fingerprints for individual records within a block of data of the core database identified by the block number; and
  send a response to the first medical imaging system, via the REST interface, including any records of the block of data of the core database missing from the first medical database and fingerprints of any records of the block of data of the first medical database missing from the core database, identified via the comparing.

18. The system of claim 15, wherein automatically synchronizing the data stored on the core database with data stored on each medical database using the REST interface comprises receiving data from the first medical database and pushing the data from the first medical database to each remaining medical database using the REST interface.

19. The system of claim 15, wherein the instructions are executable to automatically synchronize only a single block of data with a selected medical database at a time.

20. The system of claim 15, wherein the plurality of medical imaging systems comprises a plurality of computed tomography scanners.

* * * * *